United States Patent
Vujanic et al.

(10) Patent No.: US 6,290,675 B1
(45) Date of Patent: Sep. 18, 2001

(54) DEVICE FOR WITHDRAWING A CATHETER

(75) Inventors: Aleksandar Vujanic; Ali Hassan; Dragan Petrović; Werner Brenner; Dietmar Glogar, all of Vienna (AT)

(73) Assignee: EndoSonics Corporation, Rancho Cordova, CA (US)

( * ) Notice: Subject to any disclaimer, the term of this patent is extended or adjusted under 35 U.S.C. 154(b) by 0 days.

(21) Appl. No.: 09/331,951

(22) PCT Filed: Jan. 9, 1998

(86) PCT No.: PCT/EP98/00151

§ 371 Date: Nov. 2, 1999

§ 102(e) Date: Nov. 2, 1999

(87) PCT Pub. No.: WO98/30266

PCT Pub. Date: Jul. 16, 1998

(30) Foreign Application Priority Data

Jan. 9, 1997 (AT) ................................. GM 14/97

(51) Int. Cl.[7] .................................................. A61M 5/178
(52) U.S. Cl. ................ 604/159; 604/164.07; 604/164.13
(58) Field of Search .................................... 604/411, 164, 604/264, 523, 159, 280, 96.01

(56) References Cited

U.S. PATENT DOCUMENTS

| 3,835,854 | * | 9/1974 | Jewett ................................. 604/160 |
| 4,233,991 | | 11/1980 | Bradley et al. . |
| 4,729,384 | * | 3/1988 | Bazenet ............................... 604/103 |
| 5,084,010 | * | 1/1992 | Plaia et al. ........................... 604/22 |
| 5,318,541 | * | 6/1994 | Viera et al. .......................... 604/164 |
| 5,827,241 | * | 10/1998 | Douk et al. .......................... 604/523 |

FOREIGN PATENT DOCUMENTS 1000685  12/1996 (NL) .

* cited by examiner

Primary Examiner—Anhtuan T. Nguyen
Assistant Examiner—Michael Thompson
(74) Attorney, Agent, or Firm—Leydig, Voit & Mayer, Ltd.

(57) ABSTRACT

A device is disclosed for withdrawing a catheter or a probe from a body cavity or a body vessel with a drive which preferably is a friction drive and engages the axially movable part of the catheter. The drive is formed by at least one roller which is mounted for rotation around a shaft extending transversely to the direction of pull, which roller cooperates with at least one spring-loaded counter-roller, the rollers enclosing the catheter or the probe, with at least one roller being connected to a driving motor.

20 Claims, 1 Drawing Sheet

DEVICE FOR WITHDRAWING A CATHETER

This application is a national phase application based upon corresponding PCT application PCT/EP98/00151 filed on Jan. 9, 1998 (WO 98/30266), which is in turn based upon Austrian application GM 14/97 filed on Jan. 9, 1997 from which priority is claimed.

FIELD OF THE INVENTION

The invention relates to a device for withdrawing a catheter or a probe from a body cavity or a body vessel, with a drive which is preferably a friction drive and engages the axially movable part of the catheter.

BACKGROUND OF THE INVENTION

Catheters or probes are increasingly used in invasive medicine. Such catheters or probes enable body cavities or the vascular system to be analyzed or treated, e.g. intravascular ultrasonic probes being used in diagnostic medicine. While classical angiography only enables changes in longitudinal section and in particular stenoses in blood vessels to be identified, information about the condition of vascular walls can be successfully obtained with such intravascular ultrasonic catheters. In particular, information about calcification, lipoid or fibrotic structures of vascular walls can be obtained with such intravascular ultrasonic catheters, which information in particular serves as a check following interventions, such as, e.g., a stent implantation, to determine whether there are vascular wall injuries or not. Besides intravascular ultrasonic catheters, in which at least one piezoelectric crystal is arranged at the probe head to obtain an image, probes have already been used for treatment, such as, e.g., for intravascular radiation. When a so-called imaging catheter is equipped with only one crystal to obtain an image of the internal wall of a vessel, it is required for completely imaging the vascular wall to rotate this catheter about its axis during withdrawal, so that the image can be obtained as a spirally developed view of the vascular wall. Besides a regulated or constant number of revolutions, a regulated or constant speed during withdrawal of the catheter is a prerequisite. Besides such rotatably driven imaging catheters, there are also known structures having a plurality of crystals which are scanned in a corresponding phase. In such so-called "phased array" catheters, the rotation of the catheter can be omitted. However, an unavoidable prerequisite for a reproducible evaluation of the images is again a defined, in particular constant driving speed during withdrawal of the catheter. For intravascular radiations, too, a uniform feed is essential for the exact dosage. Moreover, during the uniform feed a concentration or ion gradient can be determined in vessels and organs.

The hitherto known devices for withdrawing catheters are relatively heavy and large. In rotating intravascular ultrasonic catheters the heavy motor required for rotational drive is then placed in a corresponding holding device and moved in the longitudinal direction of the catheter together with the axially movable part of the catheter. At the operating table there is hardly any room for such large and heavy devices, so that their handling is relatively laborious. Moreover, such devices usually cannot be sterilized without additional measures, and it is therefore necessary to use them in a corresponding sterile package, which further complicates their handling. Moreover, these known heavy and large devices are very expensive and usually can only be used in connection with a specific drive, e.g. for an intravascular ultrasonic catheter.

NL 10 00 685 C2 shows and describes a device for the controlled movement of a catheter, which comprises a resilient frame open on one side, in which a driving device connected with one end of the frame, such as, e.g., an arm or a pinion, cooperates with the catheter passed into openings in the frame. The frame is compressed manually, with the catheter being moved through the driving device. An adjusting screw enables the compression to be limited and thus a defined stroke and a defined path of movement of the catheter to be adjusted. Additionally, electric contacts are provided at the frame, with which a signal corresponding to the movement of the catheter can be produced during the compression of the frame.

U.S. Pat. No. 4,233,991 A shows and describes a device for withdrawing a urethral catheter, which comprises withdrawing the catheter through a spindle drive connected to a motor. The catheter is connected to the spindle drive via clamping devices.

SUMMARY OF THE INVENTION

The object of the invention is to provide a small and multi-purpose device for withdrawing a catheter, which enables different catheters to be safely driven for different purposes in the same way so as to withdraw the catheter. Besides very small sizes, the device according to the invention must also enable a correspondingly simple handling and be adaptable to different catheters or probes without extensive adaptations. To achieve this object, the device according to the invention essentially consists in that the drive comprises at least one member, which is mounted on a shaft or the like extending transversely to the direction of pull, which member cooperates with at least a counter-member, such that in operation the catheter or probe is held between said members, and that said at least one member is connected to a driving means for actuating said at least one member. In a preferred embodiment of the device according to the invention the drive is formed by at least one roller which is mounted for rotation around a shaft extending transversely to the direction of pull, which roller cooperates with at least one spring-loaded counter-roller, the rollers enclosing the catheter or the probe, and the at least one roller is connected to a driving motor. Owing to the fact that a friction drive is used, in which the withdrawable part of the catheter or the probe is gripped and conveyed between at least two rotating rollers, a substantially shorter and smaller device can be used for any path of movement when withdrawing a catheter or a probe, while the separate simultaneous rotational movement of such a withdrawing part is not adversely affected. Owing to the fact that one of the rollers is pressed in a spring-loaded fashion against at least one driven roller, the feeding or withdrawing movement of the catheter can be controlled in a very exact manner, while also the driving motor and, if required, the energy supply can be accommodated in the correspondingly small device. In principle, this drive can also be a crawler drive or, e.g., a drive with a driven roller which cooperates with two spring-loaded rollers, so as to obtain as gentle a friction engagement as possible, with a high transmission of pull.

The structure is advantageously of such a type that the driving motor is connected to the roller or rollers via a driving gear. Thus the requirements can be met with very small driving motors which rotate at a correspondingly higher number of revolutions, while the force required for withdrawing the catheter is guaranteed by the gear reduction.

The object of providing a small device is guaranteed in a very simple,manner in that the axis of the driving motor is arranged substantially parallel to the direction of pull in a housing carrying the rollers and that the roller or rollers is or are driven via a spindle drive with a shaft crossing the axis or axes of the roller or rollers. In such a structure the total drive for withdrawing a catheter or a probe can be accommodated in a very small housing, which device, in view of its simple structure, can be formed as a disposable device at correspondingly low cost. For repeated use of the same drive, a sterilization should be effected. The use of a spindle drive also permits the arrangement of a very small driving gear. In a a small housing several transmission steps can be provided between the driving motor and the spindle, so that a correspondingly large gear reduction can be achieved between the motor and the driving spindle, as a result of which the normally desired linear driving speed can be exactly maintained between 0.25 and 1 mm/sec.

In view of the small sizes the structure can advantageously be of such a type that the driving motor is connected to a power source disposed in the housing, which power source may be, e.g., a battery or an accumulator. The battery or accumulator may be arranged in a handle which can be connected to the housing with the drive for the movable part of the catheter or the probe.

The rate of feed or the rate of withdrawal can be adjusted in a very simple manner such that the driving motor is connected to the power source via a step switch arranged in the housing.

To further facilitate the handling of the device, the structure is advantageously of such a type that the housing has a swing cover, in which at least one roller or grabjaw is mounted. In such a structure the housing must only be swung open and the withdrawable part of the catheter or the probe is placed on one of the rollers or grabjaws, following which the desired pressure for the friction drive is obtained directly after closing of the housing. The stationary part, such as, e.g., the catheter casing, can preferably be supported on an abutment of the housing. The structure is preferably of such a type that the housing has a channel crossing the drive for receiving the catheter or the probe. In addition to such a channel, into which the opposite rollers, grabs or like means enter, a further parallel channel for fixing a further catheter or other stationary parts of the catheter can be provided, while the total device can be arranged in any place without separate fixing. In view of the small sizes and low cost, the drive can also directly integrate into the catheter, which may further facilitate the handling. Besides electromagnetic motors, piezoelectric magnetostrictive motors or spring motors can be advantageously used. An ultrasonic motor can also be arranged directly in or at a roller. After opening the housing, a rapid return movement of the catheter is made possible, while the motor control can be preset in any manner. Besides preferably at least two speeds different from each other, the control of the motor can be made dependent on a series of further measuring parameters, with which, e.g., contractions of muscles, e.g. the pulse beat, can be considered. The length over which the catheter must be withdrawn can be simply limited over the switching time of the motor, which is particularly advantageous for the local limitation of the desired image recording. To ensure that the desired feed was actually obtained within the given time and to check or regulate the function of the friction drive, the structure is preferably of such a type that a recording device is provided for, in particular optical or magnetic, markings, arranged at the axially movable part of the catheter, for monitoring or regulating the drive. In view of the very small structure, a sterilization of the device can also be obtained in a substantially simpler manner than in the known devices.

The device according to the invention can be adapted to different catheters without additional component parts, because it suffices to support the enveloping tube on an abutment of the housing.

BRIEF DESCRIPTION OF THE DRAWINGS

The invention will hereinafter be explained in more detail with reference to a practical example diagrammatically shown in the drawings. In these drawings

DETAILED DESCRIPTION OF THE DRAWINGS

Figure 1:
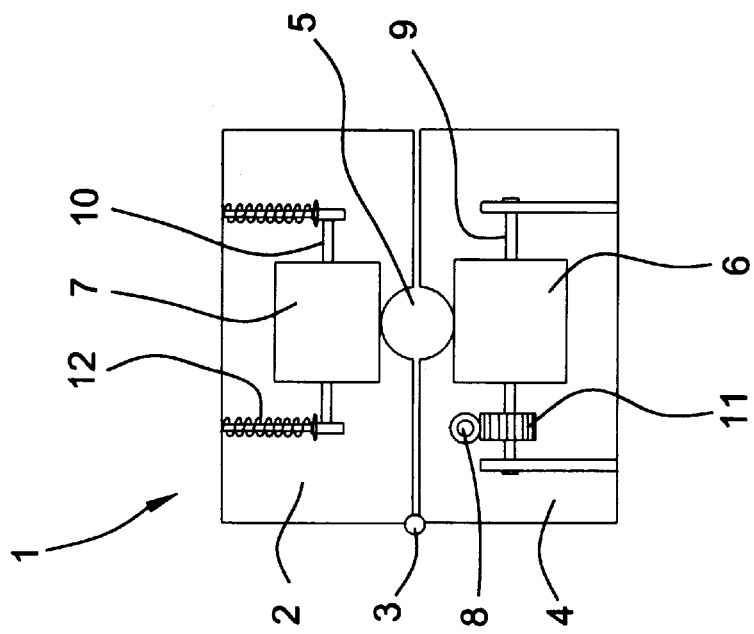
FIG. 1 shows a front view of an embodiment of the device according to the invention, partly in cross-section.

FIG. 1 shows a housing 1, the cover 2 of which is hinged to the lower part 4 of the housing on a hinge 3. Formed between the cover 2 and the lower part 4 of the housing is a channel 5, in which the withdrawable part of the catheter or the probe is placed. Cooperating with the part placed in this channel 5 are two rollers 6 and 7, of which the roller 6, which is mounted for rotation in the lower part 4 of the housing, is connected to a drive derived from a spindle 8. The rollers 6 and 7 are mounted for rotation around shafts 9 and 10, each orthogonally crossing the axis of the channel 5. In the chosen structure, only one of the rollers 6 are driven, with the spindle 8 meshing with a pinion 11, which is connected to the roller so as to be secured against rotation. The opposite roller 7 is pressed via springs 12 against the part of the catheter received in the channel 5. Besides this channel 5, there may be provided further parallel channels, not shown, for catheters to be stationarily held. The withdrawable part of the catheter is then placed by swinging open the cover 2 around the pivot pin of the hinge 3, after which the pressure required for the friction drive between the rollers 6 and 7 is obtained directly after closing.

Figure 2:
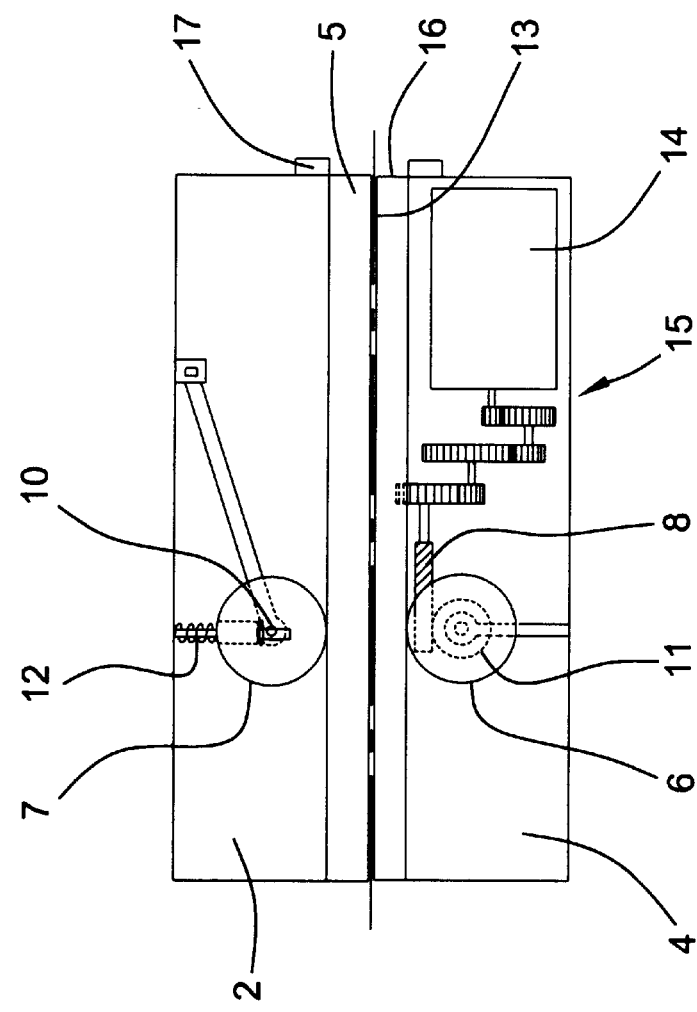
FIG. 2 shows a side view of the device shown in FIG. 1, likewise partly in cross-section.

In FIG. 2, the reference numerals of FIG. 1 were maintained. Moreover, it can be seen that the driving motor 14 is arranged in the lower part 4 of the housing parallel to the axis 13 of the channel 5. This driving motor is connected to the spindle 8 via a multi-step reduction gear 15. The driving motor 14 is an electric motor and is connected to a battery, not shown, which is arranged, e.g., in a handle portion for the lower part 4 of the housing. The handle portion may also contain the switch, not shown, in particular the multi-step reduction gear for adjusting different speeds as well as a corresponding electronic device which controls the feed or withdrawal of the movable part of the catheter. Provided at the inlet end 16 for the catheter is an abutment 17 for supporting the stationary part of the catheter, thus enabling the use of catheters of different sizes or adaptations.

What is claimed is:

1. A system for withdrawing a catheter from a body, the system comprising:
    a catheter;
    a device for withdrawing the catheter from the body comprising:
        a housing; and
        a friction drive engaging an axially movable part of the catheter, wherein the friction drive comprises:
        at least one roller mounted for rotation around a shaft extending transversely to a direction of pull, the roller being driven by a driving motor, for at least withdrawing the catheter at a controlled speed over a portion of the body, and
        at least one spring-loaded counter-roller, which cooperates with the at least one roller to engage at least the catheter.

2. A system according to claim 1, wherein the diving motor is connected to the at least one roller via a driving gear.

3. A system according to claim 1, wherein the axis of the driving motor is arranged substantially parallel to the direction of pull in the housing carrying the rollers, and that the at least one roller is driven via a spindle drive with a shaft crossing the axis of the at least one roller.

4. A system according to claim 1, wherein the driving motor is connected to a power source arranged in the housing.

5. A system according to claim 4, wherein the driving motor is connected to the power source via a step switch arranged in the housing.

6. A system according to claim 5, wherein the housing further comprises a swing cover, in which the at least one counter-roller is mounted.

7. A system according to claim 6, in the housing further comprises a channel crossing the friction drive for receiving at least the catheter.

8. A system according to claim 7, further comprising:
- an abutment of the housing, arranged for supporting a stationary part of the catheter.

9. A system according to claim 8, further comprising:
- a recording device for monitoring and regulating the friction drive, the recording device, when in operation, being responsive to markings arranged at the axially movable part of the catheter.

10. A system for withdrawing a catheter from a body, the system comprising:
- a catheter;
- a device for withdrawing the catheter from the body comprising:
  - a drive engaging an axially movable part of at least the catheter, wherein the drive comprises:
  - at least one member mounted on a shaft extending transversely to a direction of pull that is connected to a driving means for actuating the at least one member;
  - at least a spring loaded counter-roller, which cooperates with the at least one member such that at least the catheter is held between the members; and
  - an axis of the driving means arranged substantially parallel to the direction of pull for withdrawing at least the catheter at a controlled speed over at least a portion of the body.

11. A device for withdrawing a catheter from a body, the device comprising:
- a housing including an opening allowing passage of a catheter into the device; and
- a friction drive means for engaging an axially movable part of the catheter, wherein the friction drive means comprises;
  - at least one roller mounted for rotation around a shaft extending transversely to a direction of pull, the roller being driven by a driving motor, for at least withdrawing the catheter at a controlled speed over a portion of the body, and
  - at least one spring-loaded counter-roller, which cooperates with the at least one roller to engage at least the catheter.

12. A device according to claim 11, wherein the driving motor is connected to the at least one roller via a driving gear.

13. A device according to claim 11, the driving motor having an axis, wherein the axis of the driving motor is arranged substantially parallel to the direction of pull in the housing carrying the rollers, and that the at least one roller is driven via a spindle drive with a shaft crossing the axis of the at least one roller.

14. A device according to claim 11, wherein the driving motor is connected to a power source arranged in the housing.

15. A device according to claim 14, wherein the driving motor is connected to the power source via a step switch arranged in the housing.

16. A device according to claim 15, wherein the housing further comprises a swing cover, in which the at least one counter-roller is mounted.

17. A device according to claim 16, wherein the housing further comprises a channel crossing the friction drive for receiving at least the catheter.

18. A device according to claim 17, further comprising:
- an abutment of the housing for supporting a stationary part of the catheter.

19. A device according to claim 18, further comprising:
- a recording device for monitoring and regulating the friction driving means, the recording device, when in operation, being responsive to markings arranged at the axially movable part of the catheter.

20. A device for withdrawing a catheter from a body, the device comprising:
- a friction drive means for engaging an axially movable part of at least the catheter, wherein the friction drive means comprises:
  - at least one member means mounted on a shaft extending transversely to a direction of pull that is connected to a driving means for actuating the at least one member;
  - at least one counter-member means, which cooperates with the at least one member means such that at least the catheter is held between the members means; and
  - an axis of the driving means arranged substantially parallel to the direction of pull for withdrawing at least the catheter at a controlled speed over at least a portion of the body.

* * * * *